United States Patent
Boese

(10) Patent No.: US 6,493,080 B1
(45) Date of Patent: Dec. 10, 2002

(54) ATR MEASURING CELL FOR FTIR SPECTROSCOPY

(75) Inventor: Matthias Boese, Karlsruhe (DE)

(73) Assignee: Bruker Optik GmbH, Ettlingen (DE)

( * ) Notice: Subject to any disclaimer, the term of this patent is extended or adjusted under 35 U.S.C. 154(b) by 1 day.

(21) Appl. No.: 09/643,934

(22) Filed: Aug. 23, 2000

(30) Foreign Application Priority Data

Oct. 16, 1999 (DE) .......................................... 199 49 953

(51) Int. Cl.⁷ ............................ G01N 1/10; G01N 21/01
(52) U.S. Cl. ......................................... 356/246; 356/244
(58) Field of Search ................................. 356/244, 246, 356/36, 300, 302, 326, 331; 250/304, 341.1; 422/82.09, 82.05, 82.11, 68.1, 66, 67; 435/808

(56) References Cited

U.S. PATENT DOCUMENTS

| | | | |
|---|---|---|---|
| 5,350,923 A | * 9/1994 | Bassignana et al. ... | 250/453.11 |
| 5,362,445 A | 11/1994 | Miyahara | |
| 5,846,842 A | * 12/1998 | Herron et al. ............... | 436/518 |
| 6,222,619 B1 | * 4/2001 | Herron et al. ................. | 356/39 |

FOREIGN PATENT DOCUMENTS

| | | |
|---|---|---|
| DE | 42 28 070 | 3/1994 |
| DE | 44 26 944 | 2/1996 |
| DE | 196 12 877 | 9/1997 |
| GB | 2 228 083 | 8/1990 |

\* cited by examiner

Primary Examiner—Michael P. Stafira
(74) Attorney, Agent, or Firm—Paul Vincent

(57) ABSTRACT

A total reflection measuring cell for the spectroscopic examination of a sample in an IR spectrometer comprising an ATR crystal (1) having a plane surface (2) and a diaphragm clamped in a clamping frame (13) is characterized in that, additionally a tensioning device is provided for parallel displacement of the diaphragm on an inner partial area of its surface clamped between the legs of the clamping frame (13) in the direction of the plane surface (2) of the ATR crystal (1) that the displaced inner partial area of the diaphragm surface has a higher tension than the clamped diaphragm surface merely clamped in the clamping frame (13) before, and that a stop is provided towards which the tensioning device is forced and fixed in that position such that the inner partial area of the diaphragm surface has always the same defined separation from the plane surface (2) of the ATR crystal (1). In this fashion, it is possible to exactly keep the separation from the plane surface (2) of the ATR crystal (1) despite the tendency of the diaphragm to form waves or sag. The otherwise caused quantitative measuring errors due to waviness or displacement of the diaphragm in the IR spectrum can be prevented and thus a considerably higher measurement accuracy can be guaranteed and the quality of the measurement results can be reliably ensured.

22 Claims, 4 Drawing Sheets

ATR MEASURING CELL FOR FTIR SPECTROSCOPY

This application claims Paris Convention priority of DE 199 49 953.5 filed Oct. 16, 1999 the complete disclosure of which is hereby incorporated by reference.

BACKGROUND OF THE INVENTION

The invention concerns a total reflection measuring cell for the spectroscopic examination of an, in particular, fluid sample in an infrared (=IR) spectrometer comprising an ATR (=attenuated total reflectance) crystal having a plane surface and a diaphragm clamped on several sides in a clamping frame, wherein the clamping frame is disposed such that the diaphragm extends at a small separation from the plane surface of the ATR crystal.

ATR measuring cells of this type are known from U.S. Pat. No. 5,362,445 A1 or DE 196 12 877 C1.

To study the interactions between biomolecules by means of FTIR-ATR spectroscopy, it is important to introduce ligands in the evanescent field without causing mechanical disturbances of the sensitive layer on the ATR crystal or changing the concentrations of the dissolved substances which interact with the immobilized molecules. This is realized by a diaphragm, generally a dialysis diaphragm which is disposed above the sensitive crystal surface and separates a sample chamber below the diaphragm from a dialysis chamber above the diaphragm. Compounds having a low molecular weight can be dialyzed into and out of the sample chamber according to the MW Cut-Off of the diaphragm without lessening macromolecules in the evanescent field or destroying the immobilized thin layers on the crystal surfaces. Introduction of the ligands into the evanescent field can be accelerated beyond the thermal diffusion rate. Through the use of electrophoretical currents, charged ligands can be specifically transported into and out of the sample chamber through the diffusion barrier and the mechanical obstacle formed by the dialysis diaphragm.

The construction and use of such total reflection measuring cells through the initially mentioned features is described in detail in the above cited DE 196 12 877 C1, the complete disclosure of which is hereby incorporated by reference. The use of a diaphragm in an ATR cell includes, however, the problem of keeping an exact distance from the plane surface of the ATR crystal. Unfortunately, the diaphragms clamped in a clamping frame have generally the tendency to form waves or sag through. The filling or emptying of the hollow space above the diaphragm can cause pressure transfer to the hollow space below the diaphragm such that the sensitive sample layer on the crystal is damaged and the IR measurement becomes impossible. In the extreme case, the diaphragm will sag that much that during filling/removing processes it comes even in direct contact to the crystal surface thus removing the immobilized sample from the crystal.

It is therefore the object of the present invention to present a total reflection measuring cell of the initially mentioned type which does not have the above-mentioned disadvantages, guarantees a considerably increased measuring accuracy and thus reliably ensures the quality of the measuring results.

SUMMARY OF THE INVENTION

In accordance with the invention, this is achieved by additionally providing a tensioning device for displacing the diaphragm on an inner partial area of its surface clamped between the legs of the clamping frame in the direction of the plane surface of the ATR crystal such that the displaced inner partial area of the diaphragm surface has a higher tension than before the diaphragm surface merely clamped in the clamping frame, and providing a stop to which the tensioning device is forced and fixed in this position such that the inner partial area of the diaphragm surface has an identical defined distance from the plane surface of the ATR crystal.

The tensioning device reliably prevents sagging of the diaphragm in the tensioned inner partial area such that the natural waviness of the diaphragm material does not present any problems any more. The mechanical stop achieves an extremely exact positioning of the tensioned diaphragm surface in the inner partial area relative to the plane surface of the ATR crystal, in particular an exact parallelism with simple means and without great production effort.

Particularly preferred is an embodiment of the inventive ATR measuring cell wherein the tensioning device comprises a continuous wedge whose continuous closed edge line tensions the inner partial area of the diaphragm and forces same towards the ATR crystal. A continuous wedge of this type can be produced in a mechanically simple manner and with high accuracy.

In an advantageous further development of this embodiment, the angle of the wedge sides of the continuous wedge towards the plane surface of the ATR crystal in the fixed position of the tensioning device is between 30° and 60°, preferably approximately 45°. In general, one will choose a symmetrical wedge shape, i.e. both wedge sides having the same angle. Variants are also feasible wherein the two wedge sides have different angles.

Due to the longitudinal shape of the common ATR crystals, a further development is preferred wherein the continuous enclosed edge line of the continuous wedge forms a longitudinal oval comprising two parallel longitudinal sides forming a semi-circle at each of their ends.

One embodiment is particularly preferred, wherein the stop towards which the tensioning device can be forced and fixed in this position comprises a continuous inclined surface of an inclination corresponding to the wedge angle. This guarantees positioning of the diaphragm tensioned in the inner partial area plane-parallel to the sensitive surface of the ATR crystal with high precision whereby the production effort is very small.

A further advantageous embodiment of the inventive ATR measuring cell is characterized in that between the inner partial area of the tensioned diaphragm surface within the continuous enclosed edge line of the continuous wedge and a cover part of the tensioning device facing away from the diaphragm in the unfolded state, a hollow volume is formed which can be filled or emptied via an inlet and an outlet in the cover part. The sample fluid can flow through this hollow space when fluid samples are measured.

A further development is advantageous, wherein the cover part is produced from transparent material, preferably plexiglass. This allows in particular observation of the flow behaviour of the sample fluid but also discovery of possible contamination in the hollow space and removal thereof through rinsing.

Also preferred is one embodiment wherein a hollow volume is formed between the plane surface of the ATR crystal and the tensioned inner partial area of the diaphragm surface which can be filled or emptied via an inlet and an outlet. In this manner, the molecules diffused through the diaphragm can contact the sensitive surface of the ATR crystal. Moreover, the inlet and outlet allow rinsing of the sensitive area of the ATR crystal for cleaning which may serve i.a. to prepare subsequent measurements.

One embodiment of the inventive ATR cell is particularly preferred wherein the tensioning device can be detachably and rigidly connected, preferably screwed to a base plate onto which the ATR crystal is fixed. This considerably facilitates the relative positioning and fixing of the achieved optimum position between diaphragm and ATR crystal.

One further development of this embodiment is particularly preferred for geometrical reasons, wherein the inlet and outlet lead, through the base plate, to the hollow space between the plane surface of the ATR crystal and the tensioned inner partial area of the diaphragm surface.

In a further development, the optimum relative position can be achieved and fixed in that the clamping frame comprising the clamped diaphragm is disposed between the base plate and the tensioning device and comprises through-bores for receiving and guiding the screws for screwing the tensioning device to the base plate.

In a particularly simple further development of these embodiments, the stop for the tensioning device is integrated in the base plate.

One further development is particularly advantageous with respect to handling of the respective individual parts of the inventive ATR measuring cell, wherein the continuous inclined surface of the stop is disposed on the base plate side facing the diaphragm in the mounted state and surrounds an inside width through the base plate wherein on the other side of the base plate, the ATR crystal is fixed with its plane surface facing the inside width.

The diaphragm used in the inventive ATR measuring cell is usually formed as dialysis diaphragm. In embodiments, the ATR measuring cell itself can be formed as dialysis cell.

Alternatively, the ATR measuring cell can also be formed as electrophoresis cell.

To allow a simple possibility for both measuring methods, the inventive ATR measuring cell can be constructed such that two exchangeable cover parts can be mounted onto a fixed base plate part comprising the ATR crystal fixed thereon or thereto, wherein the cover parts contain the respectively used diaphragms with the inventive tensioning devices and are especially designed either for dialysis or electrophoresis measurements. Such an ATR measuring cell meets the most important requirements for infrared studies on a large plurality of macromolecular interactions. The unit generally contains a trapezoidal internal reflection element in the form of the ATR crystal which is disposed in a rinsable casing with regulated temperature and completely encapsulated. The base plate onto which the ATR crystal is fixed is generally advantageously coated with teflon.

In an advantageous embodiment of the inventive ATR measuring cell, a further clamping frame with clamped diaphragm and a further tensioning device are disposed on the side of the first diaphragm facing away from the ATR crystal in the mounted state, parallel and at a defined separation from same. This embodiment is suited in particular for electrophoresis examinations.

A further development of this embodiment is characterized in that both tensioning devices comprise two continuous wedges arranged next to one another and extending parallel to the ray guidance axis of the ATR crystal. Their continuous enclosed edge lines tension the respective inner partial area of the diaphragms disposed in parallel and force same towards the ATR crystal wherein the tensioning device located closer to the ATR crystal comprises on its side facing away from the ATR crystal a stop for the tensioning device further away from the ATR crystal which comprises two continuous inclined surfaces whose inclination corresponds with the wedge angle of the two continuous edge lines of the tensioning device further away from the ATR crystal.

This further development can be improved in that the two tensioning devices disposed on top of one another are formed such that when mutual fixing, the diaphragm tensioned between them is forced between the two continuous wedges of the tensioning device further away from the ATR crystal such that it represents a large Ohmic resistance in this area. This prevents undesired "cross flows" via the tensioned diaphragm.

One further development is also preferred wherein the tensioning device less remote from the ATR crystal comprises recesses within the two continuous wedges such that two hollow spaces are generated between the two unfolded diaphragms which can be separately filled via a separate inlet and a separate outlet within the tensioning device closer to the ATR crystal.

Moreover, it is favourable to generate a hollow space between the unfolded diaphragm less remote from the ATR crystal and the ATR crystal which can be filled and emptied via an inlet and an outlet within the base plate to which at least one of the two tensioning devices is mounted.

Finally, a further improvement can be achieved in that the tensioning device further away from the ATR crystal comprises recesses within the two continuous wedges which are connected in a direction opposite to the two tensioned diaphragms separately with two separate hollow spaces such that after filling all hollow spaces of the mounted ATR cell with an electrically conducting liquid and after applying an electric voltage to the hollow spaces, which are connected with the recesses of the tensioning device further away from the ATR crystal, a current flux can be generated which flows from the hollow space connected with a cathode to the hollow space connected with an anode passing both diaphragms twice.

Further advantages of the invention can be gathered from the description and the drawing. The features mentioned above and below can be used in accordance with the invention either individually or collectively in any arbitrary combination. The embodiments shown and described are not to be understood as exhaustive enumeration but have exemplary character for describing the invention.

The invention is shown in the drawing and is explained in more detail with reference to an embodiment:

DESCRIPTION OF THE PREFERRED EMBODIMENT

Figure 1:
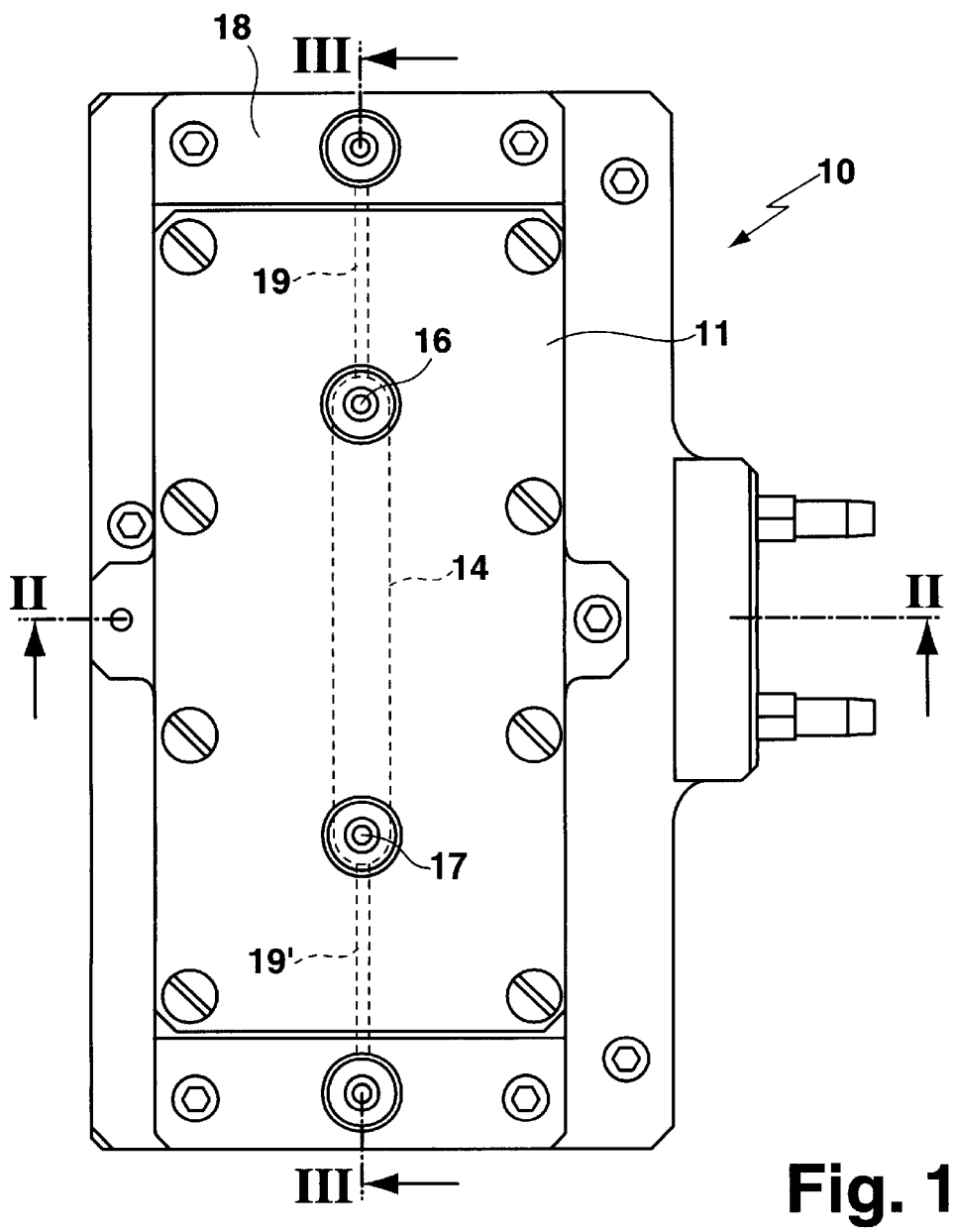
FIG. 1 shows a schematic top view of the partially transparent cover part of an inventive ATR measuring cell formed as dialysis cell.
Figure 2:
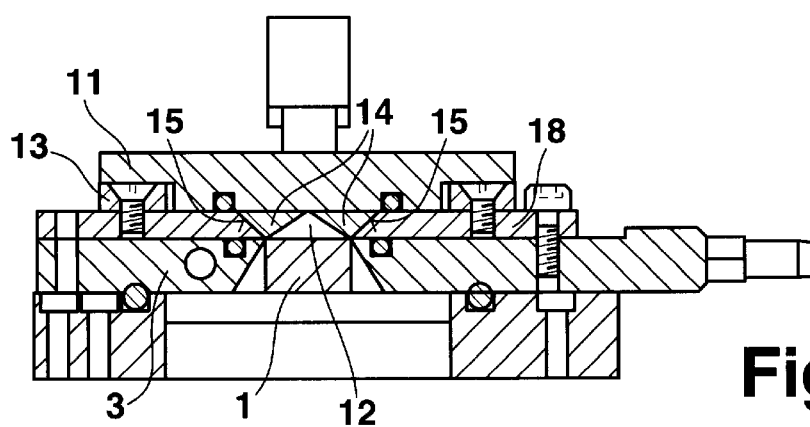
FIG. 2 shows a section along II—II of FIG. 1.
Figure 3:
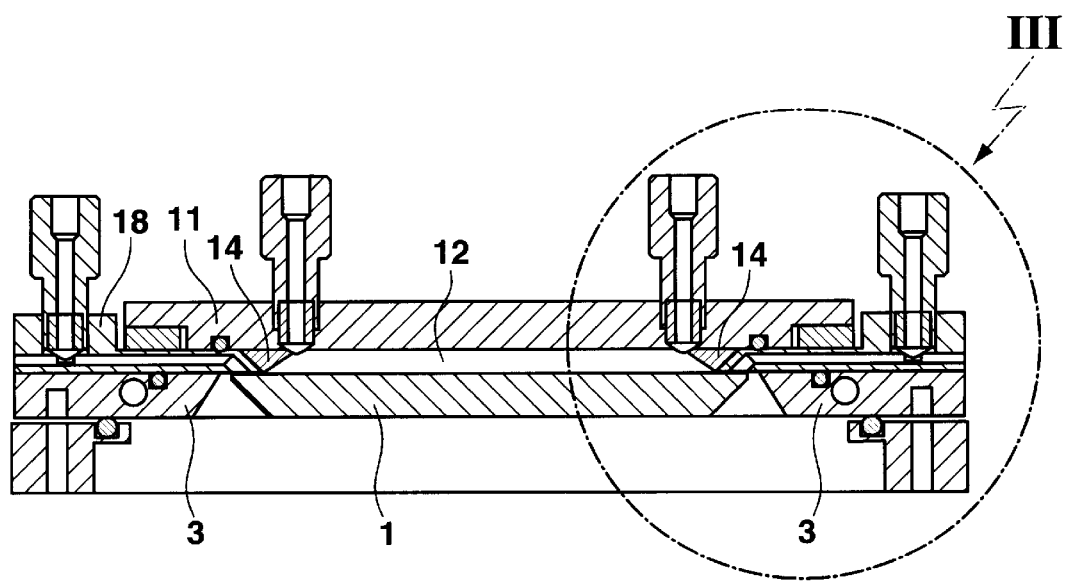
FIG. 3 shows a section along III—III of FIG. 1.
Figure 4:
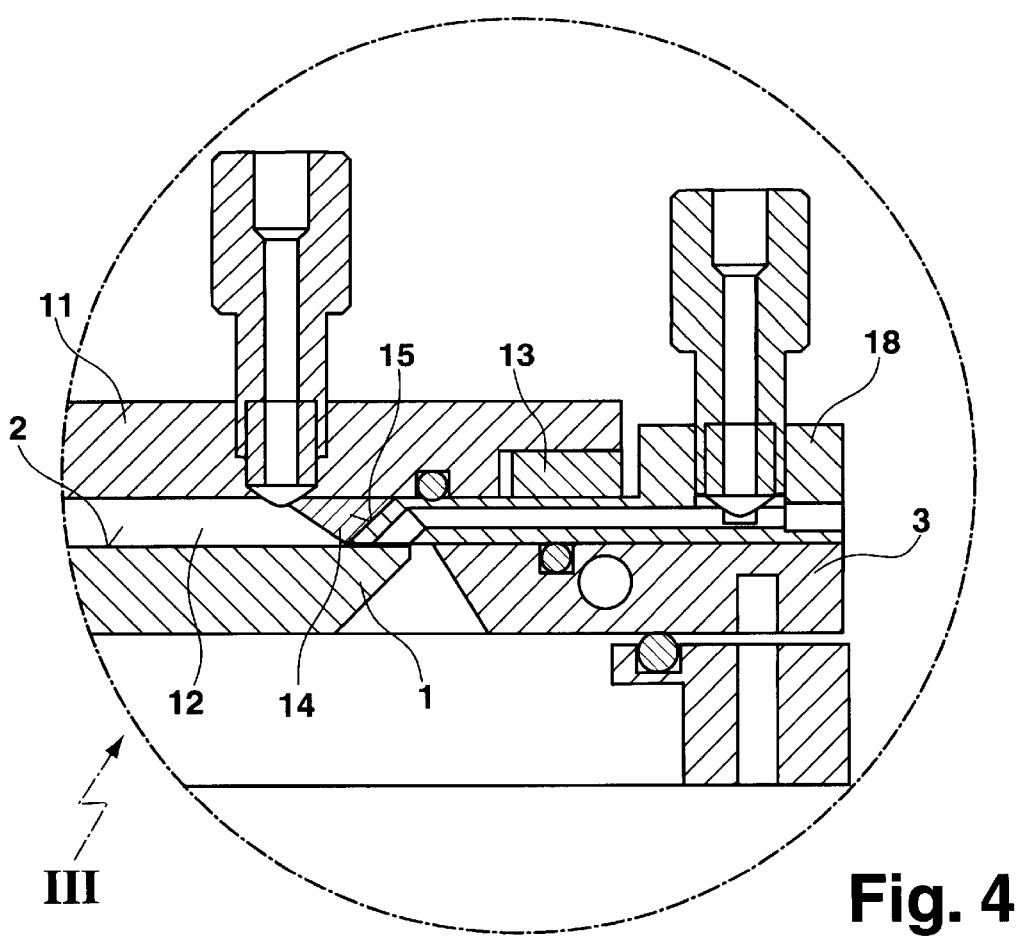
FIG. 4 shows the detail III of FIG. 3.
Figure 5:
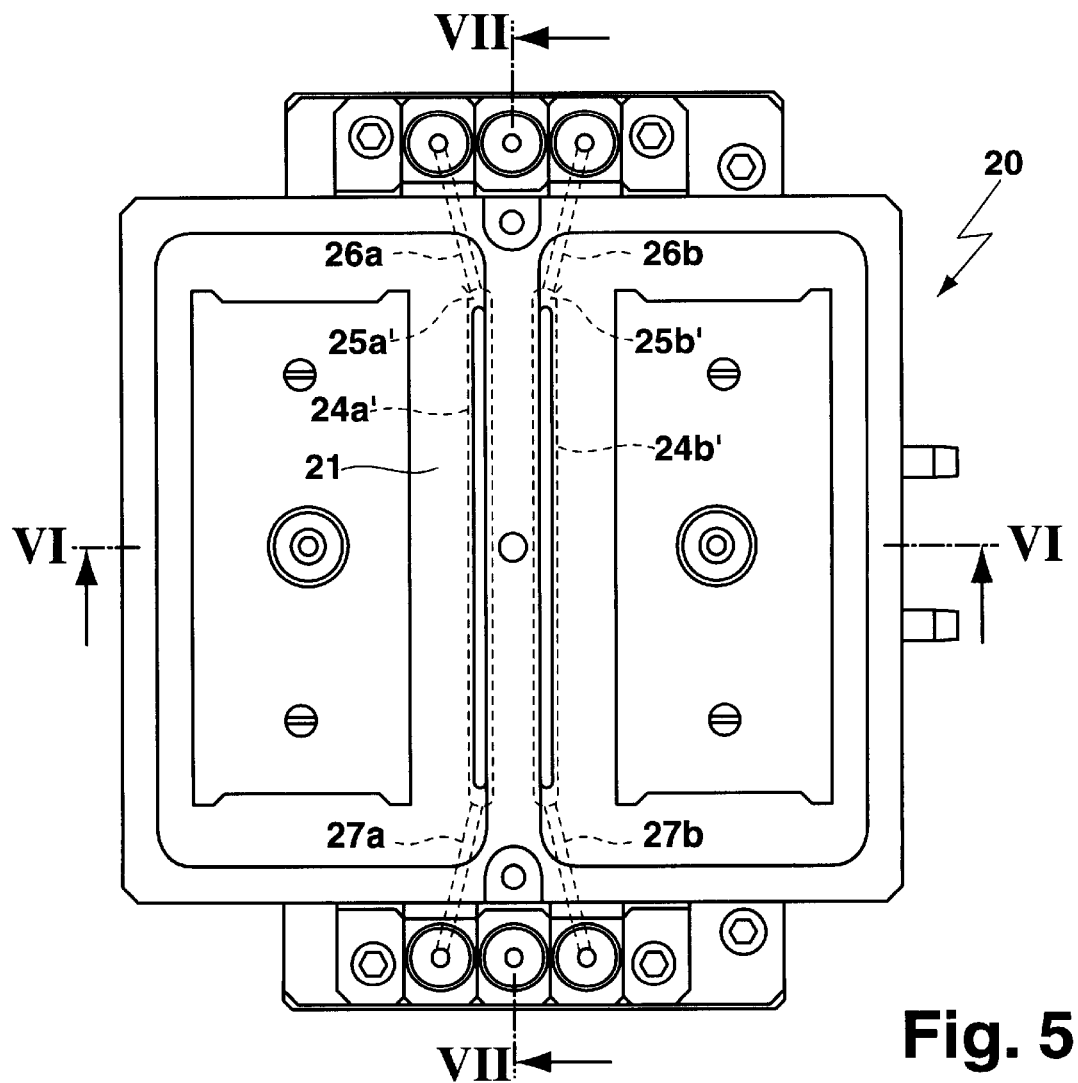
FIG. 5 shows a top view of the partially transparent cover part of an embodiment of the inventive ATR measuring cell formed as electrophoresis cell.
Figure 6:
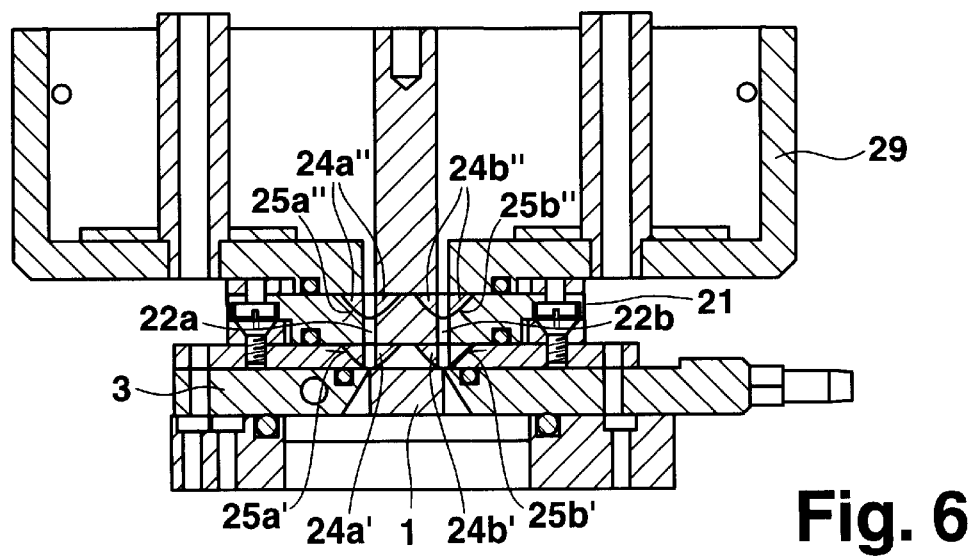
FIG. 6 shows a section along VI—VI of FIG. 5.
Figure 7:
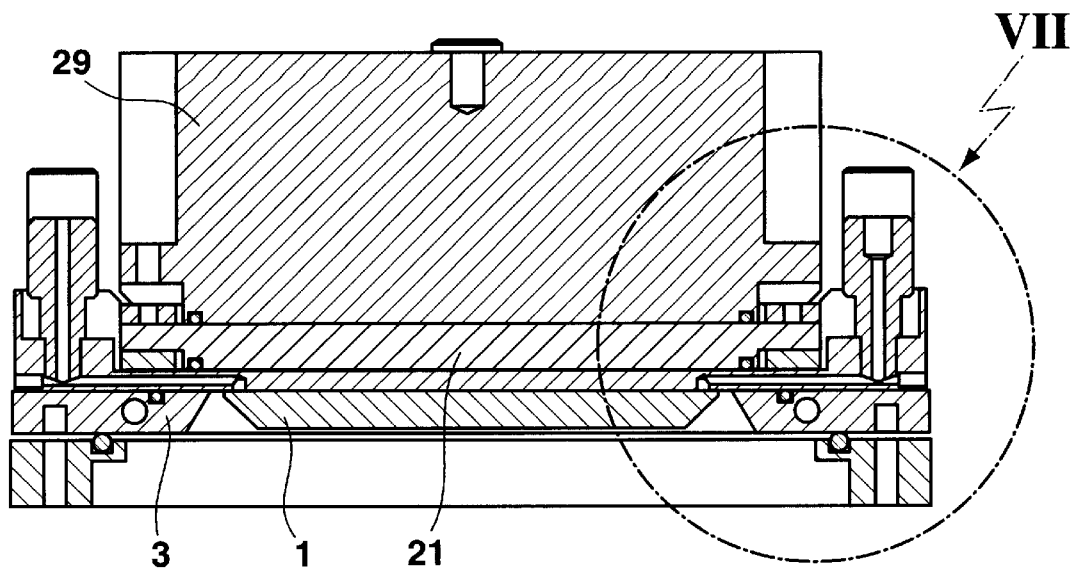
FIG. 7 shows a section along VII—VII of FIG. 5.
Figure 8:
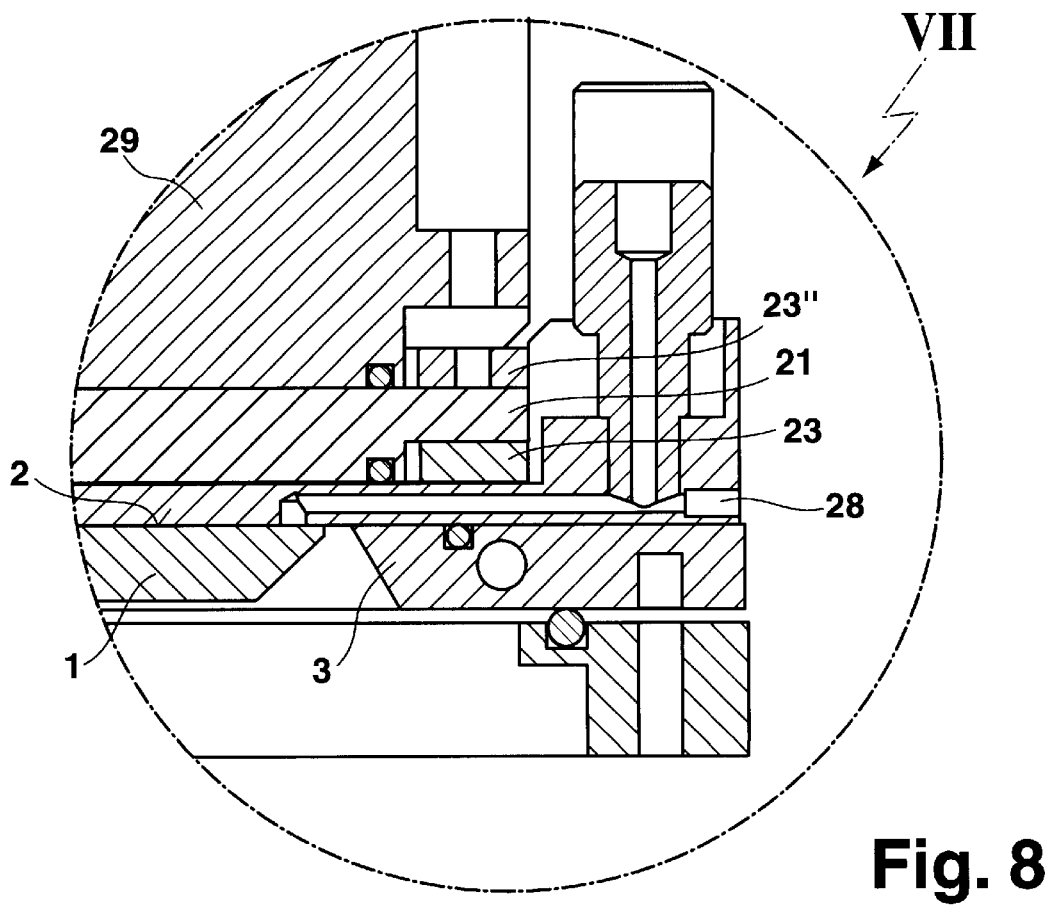
FIG. 8 shows the detail VII of FIG. 7.

FIGS. 1 to 4 show an ATR measuring cell 10 formed as dialysis cell. It contains an ATR crystal 1 having a sensitive plane surface 2 which is rigidly connected to a clamping frame 3. A thin dialysis diaphragm is mounted parallel to the plane surface 2 of the ATR crystal 1 which is clamped in a clamping frame 13 and tensioned by a tensioning device and disposed at a defined separation plane-parallel to the surface 2.

The tensioning device of the shown dialysis measuring cell 10 comprises a base plate 18 rigidly screwed with the clamping frame 3 onto which a cover part 11 of plexiglass is screwed. The clamping frame 13 with clamped diaphragm is screwed between the base plate 18 and the cover part 11. The cover part 11 comprises on its side facing the ATR crystal 1 a continuous wedge 14 whose continuous enclosed edge line forces an inner partial area of the diaphragm clamped in the clamping frame 13 in the direction of the ATR crystal 1 and thus tensions same. This guarantees that the displaced partial area of the diaphragm surface has always the same defined separation from the plane surface 2 of the ATR crystal 1.

A continuous inclined surface 15 which is integrated in the base plate serves as stop for the outer partial surfaces of the continuous wedge 14. A hollow space 12 is generated between the inner partial area of the tensioned diaphragm surface within the enclosed edge line of the continuous wedge 14 and the cover part 11 of the tensioning device which can be filled and emptied via an inlet 16 and an outlet 17, respectively.

FIG. 1 is a top view of the transparent cover part 11 in which the continuous wedge 14, the inlet 16 and the outlet 17 are indicated with broken lines.

A further hollow space is formed between the tensioned diaphragm and the plane surface 2 of the ATR crystal 1. It can also be filled and emptied, respectively, via an inlet 19 and an outlet 19'.

In the embodiment shown, the enclosed line of the continuous wedge 14 forms a longitudinal oval with two parallel longitudinal sides forming a semi-circle at each of their ends thereby achieving optimum adaptation to the longitudinal ATR crystal 1. Heating means for the ATR crystal 1 are provided which can be integrated in the clamping frame 3 and allow regulated temperature-control of the crystal.

It is also possible to mount an electrophoresis top to the clamping frame 3 with fixed ATR crystal 1 shown in FIGS. 1 to 4 which is shown in FIGS. 5 to 8. The electrophoresis cell 20 shown therein comprises, in contrast to the dialysis cell 10, two unfolded diaphragms disposed on top of one another parallel to the sensitive surface 2 of the ATR crystal 1. They are clamped between the legs of two clamping frames 23', 23" disposed in parallel on top of one another. Each of the two diaphragms comprises a tensioning device each comprising two continuous wedges 24a', 24b' and 24a", 24b", respectively. The continuous wedges 24a', 24b' which tension the diaphragm closer to the ATR crystal 1 are integrated in a cover part 21 on which is disposed a reservoir 29 which again comprises the continuous wedges 24a", 24b". The latter abut corresponding inclined surfaces 25a", 25b" on the side of the cover part 21 facing away from the ATR crystal 1. The inclined surfaces 25a', 25b' of the stops for the continuous wedges 24a', 24b' of the cover part 21 are integrate in a base plate 28 which is screwed, together with the cover part 21 and the reservoir 29, to the clamping frame 3.

The tensioning device closer to the ATR crystal 1 comprises again recesses within the two continuous wedges 24a', 24b' thereby generating two hollow spaces 22a, 22b between the two unfolded diaphragms which can be filled with fluid via separate inlets 26a, 26b and separate outlets 27a, 27b within the tensioning device closer to the ATR crystal 1.

I claim:

1. A total reflection measuring cell for spectroscopic examination of a sample in an infrared (IR) spectrometer, the measuring cell comprising:

an attenuated total reflectance (ATR) crystal having a planar surface;

a clamping frame;

a diaphragm clamped in said clamping frame along a plurality of sides to extend at a small separation from said planar surface;

a tensioning device communicating with said diaphragm for parallel displacement of an inner surface portion of said diaphragm in a direction towards said planar surface to create a displaced inner partial area of said diaphragm under higher tension; and a stop in communication with said tensioning device, said tensioning device pushed against said stop and fixed to maintain a constant defined separation between said planar surface and said displaced inner partial area.

2. The measuring cell of claim 1, wherein said tensioning device comprises a peripheral wedge having a peripheral closed edge line to tension and push said inner partial area of said diaphragm towards said planar surface.

3. The measuring cell of claim 2, wherein wedge sides of said peripheral wedge have wedge angles with respect to said planer surface of said ATR crystal, said wedge angles lying between 30° and 60° in a fixed position of said tensioning device.

4. The measuring cell of claim 2, wherein said peripheral closed edge line of said peripheral wedge forms a longitudinal oval having two parallel longitudinal sides each forming a semi-circle at their ends.

5. The measuring cell of claim 3, wherein said stop against which said tensioning device is pressed and in which position it can be fixed, has a peripheral inclined surface with an inclination corresponding to said wedge angles.

6. The measuring cell of claim 2, wherein said tensioning device comprises a cover part facing away from said diaphragm in a tensioned state, said cover part defining a hollow space between said inner partial area of tensioned diaphragm surface within said peripheral closed edge line of said peripheral wedge which can be filled and emptied via an inlet and an outlet in said cover part.

7. The measuring cell of claim 6, wherein said cover part is produced from transparent material.

8. The measuring cell of claim 5, wherein said planar surface of said ATR crystal and said displaced inner partial area of said diaphragm define a hollow space which can be filled and emptied via an inlet and an outlet.

9. The measuring cell of claim 8, further comprising a base plate on which said ATR crystal is mounted and means for rigid, detachable connection of said tensioning device to said base plate.

10. The measuring cell of claim 9, wherein said inlet and said outlet pass through said base plate into said hollow space between said planar surface of said ATR crystal and said displaced inner partial area of said diaphragm.

11. The measuring cell of claim 9, wherein said clamping frame is disposed between said base plate and said tensioning device, said clamping frame having through holes for receiving and guiding said connection means with which said tensioning device can be fastened to said base plate.

12. The measuring cell of claim 9, wherein said stop for said tensioning device is integrated in said base plate.

13. The measuring cell of claim 9, wherein said peripheral inclined surface of said stop is disposed on a side of said base plate facing said diaphragm in a mounted state to surround a through hole in said base plate, wherein said ATR crystal is fixed on another side of said base plate with said planar surface facing said through hole.

14. The measuring cell of claim 1, wherein said diaphragm is a dialysis diaphragm.

15. The measuring cell of claim 1, wherein said ATR measuring cell is a dialysis cell.

16. The measuring cell of claim 1, wherein said the ATR measuring cell is a electrophoresis cell.

17. The measuring cell of claim 1, further comprising a second clamping frame holding a second diaphragm and a second tensioning device, said second diaphragm mounted parallel to and at a defined separation from that side of said diaphragm facing away from said ATR crystal.

18. The measuring cell of claim 17, wherein said second tensioning device and said tensioning device each comprise two mutually proximate peripheral wedges disposed parallel to a ray guidance axis of said ATR crystal peripheral closed edge lines of which each tension a respective inner partial area of said parallel arranged diaphragm and of said second diaphragm to push same in a direction towards said ATR crystal, wherein said tensioning device closer to said ATR crystal comprises a second stop for said second tensioning device further removed from said ATR crystal, said second stop having two peripheral inclined surfaces having inclinations corresponding to wedge angles of said two peripheral edge lines of said second tensioning device further removed from said ATR crystal.

19. The measuring cell of claim 18, wherein said second tensioning device is disposed on top of said tensioning device such that said second diaphragm tensioned between said two peripheral wedges of said second tensioning device further removed from said ATR crystal is pressed to represent a large Ohmic resistance in this region.

20. The measuring cell of claim 19, wherein said tensioning device closer to said ATR crystal has recesses within its two peripheral wedges such that two hollow spaces are generated between said diaphragm and said second diaphragm which can be separately filled via a separate inlet and a separate outlet formed in said tensioning device closer to said ATR crystal.

21. The measuring cell of claim 20, further comprising a base plate to which at least one of said second tensioning device and said tensioning is mounted, wherein a hollow space is generated between said diaphragm closer to said ATR crystal and said ATR crystal which can be filled and emptied via an inlet and an outlet in said base plate.

22. The measuring cell of claim 21, wherein said second tensioning device disposed further away from said ATR crystal comprises recesses within said two peripheral wedges which are separately connected to two separate hollow spaces in a direction opposite to both said second diaphragm and said diaphragm such that after filling all hollow spaces of said ATR cell with an electrically conductive liquid and after application of an electric voltage to said hollow spaces connected to said recesses of said second tensioning device further away from said ATR crystal, a current flow can be generated which flows from a hollow space connected to a cathode to a hollow space connected to an anode to thereby pass said second diaphragm and said diaphragm twice.

* * * * *